United States Patent [19]

Nabai et al.

[11] Patent Number: 5,479,936
[45] Date of Patent: Jan. 2, 1996

[54] BIOPSY WOUND CLOSURE DEVICE AND METHOD

[76] Inventors: Hossein Nabai, 14555 Levan Rd., Suite 410, Livonia, Mich. 48154; Homayoon Rahbari, 1314 N. Macomb St., P.O. Box 360, Monroe, Mich. 48161

[21] Appl. No.: 358,819

[22] Filed: Dec. 19, 1994

Related U.S. Application Data

[62] Division of Ser. No. 56,399, May 4, 1993, Pat. No. 5,388,588.

[51] Int. Cl.$^6$ ............................................. A61B 5/00
[52] U.S. Cl. ................................... 128/754; 604/15
[58] Field of Search ................................... 128/749, 751, 128/753, 754; 604/11, 15, 16, 22, 51, 73, 187, 264, 272, 286

[56] References Cited

U.S. PATENT DOCUMENTS

| | | | |
|---|---|---|---|
| 5,021,059 | 6/1991 | Kensey et al. | 606/213 |
| 5,080,655 | 1/1992 | Haaga | 128/754 |
| 5,275,616 | 1/1994 | Fowler | 606/213 |

*Primary Examiner*—Max Hindenburg
*Attorney, Agent, or Firm*—Alex Rhodes

[57] ABSTRACT

A method and closure device for performing a routine biopsy procedure without the use of sutures or butterfly bandages. The method and closure device controls bleeding, repairs the biopsy site, reduces the likelihood of inducing excessive scarring and reduces the handling of tissue. The closure device is comprised of a syringe, a detachable needle mounted on an end portion of the syringe, a biopsy punch mounted on the syringe which is accessible when the needle is detached from the syringe, and a a circular sponge made from an absorbable foam material which swells and fills up the defect left by biopsy and an applicator for implanting the sponge into the biopsy site. The sponge is pre-formed to a diameter which approximately corresponds to the diameter of the punch which is used for excising a biopsy specimen. After a biopsy site has been anesthetized with the syringe and needle, the needle is removed to expose the biopsy punch, the specimen is excised with the punch and the sponge is implanted into the space from which the specimen was taken, A slight pressure is applied to the sponge for approximately 30 to 60 seconds to stop any excess bleeding.

9 Claims, 2 Drawing Sheets

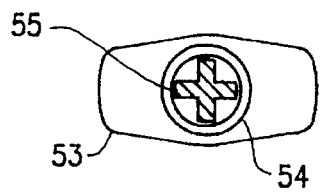
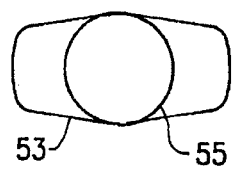
FIG. 5   FIG. 1
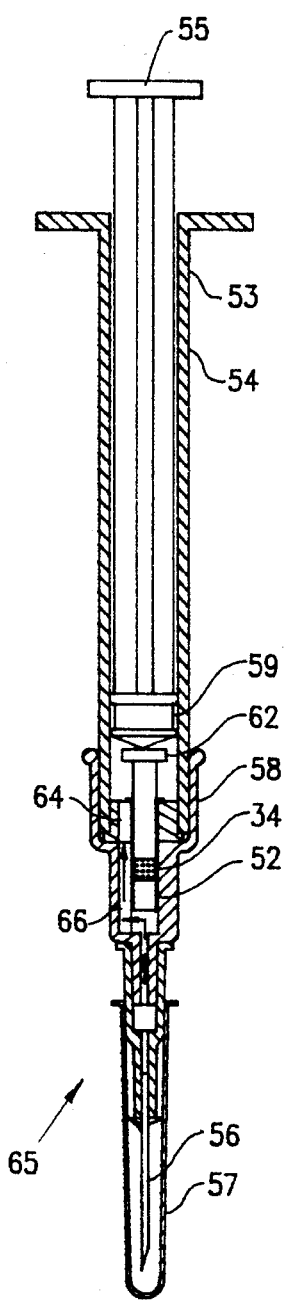
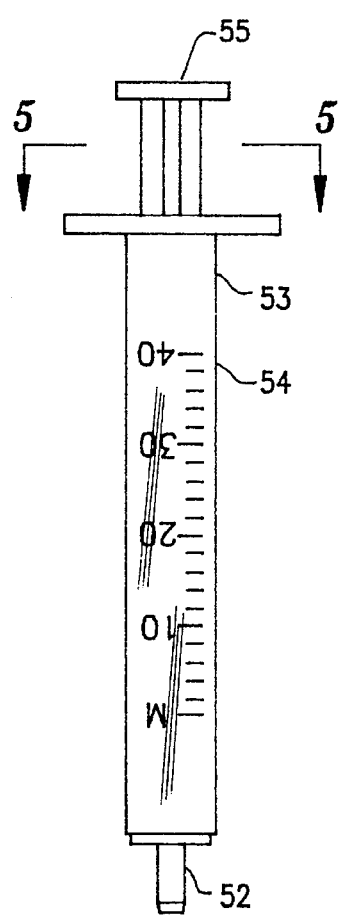
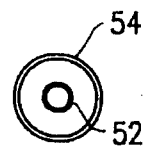
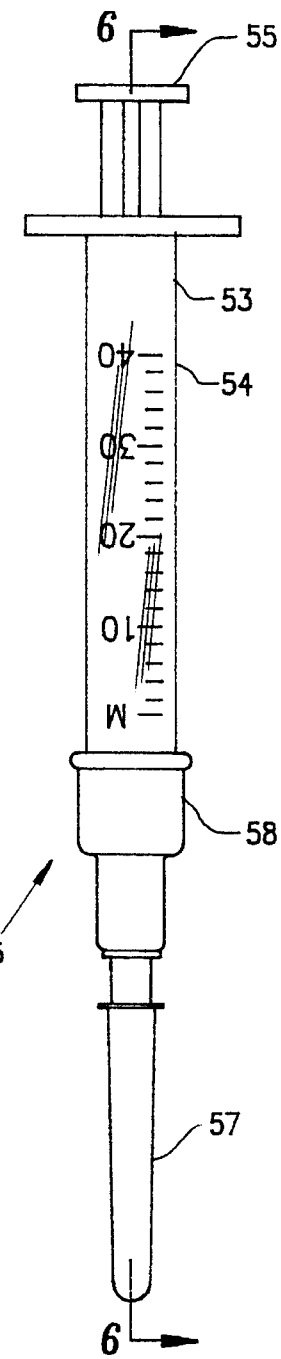
FIG. 6   FIG. 3   FIG. 4   FIG. 2

BIOPSY WOUND CLOSURE DEVICE AND METHOD

This is a divisional of application Ser. No. 08/056,399 filed on May 4, 1993, now U.S. Pat. No. 5,388,588.

BACKGROUND OF THE INVENTION

This invention relates to wound closure devices and more particularly to a biopsy wound closure apparatus and method for controlling bleeding and repair of the biopsy site during a routine skin biopsy procedure.

The skin is a complex anatomical system composed of two layers–the epidermis, or epithelium, which is visible to the naked eye, and the dermis or corium, below the epidermis which is firmly interlocked with the dermis. When the skin is punctured, the cells of the surrounding dermis and epidermis multiply to compensate for the loss of cells in the dermis and epidermis. Skin biopsies are frequently performed to diagnose abnormal skin conditions.

Surgical punches, ranging in diameter from 2 to 6 millimeters, are commonly used to excise small samples of skin for medical biopsies. The punches are razor sharp circular knives which are pressed against the skin and rotated to excise cylinder shaped samples for biopsies.

The current practice during a routine skin biopsy procedure is to use sutures, or for small wounds multiple butterfly bandages, to control the flow of blood and to repair the biopsy site. One deficiency with this practice is that some patients suffer anxiety during the suturing of wounds. Another deficiency is that a considerable amount of time is spent by physicians for hemostasis and repair of the biopsy site during routine biopsy procedures.

Sterile sponges have been used as packing material during surgery when hemostatic devices for controlling capillary, venous and arteriolar bleeding are either ineffective or impractical. However, sterile sponges have neither been available nor used to repair biopsy sites or to control bleeding during biopsy procedures. Nor have small pre-cut implant devices having the same or similar diameters as surgical punches been used to repair resulting defects or to control bleeding after excisions of specimens for skin biopsies.

In view of the foregoing, it is apparent that a more efficient, effective, easy to use apparatus and method for performing a routine biopsy procedure would satisy an existing need.

SUMMARY OF THE INVENTION

The present invention satisfies the existing need by providing a pre-cut sterile sponge and applicator for hemostasis and repair of a biopsy site during a routine biopsy procedure.

The invention is comprised of a syringe, a needle detachably mounted on a lower end portion of the syringe, a biopsy punch mounted on a lower end portion of the syringe which is accessible when the needle is detached from the syringe, and a pre-cut sterile sponge in an interior of said punch of the approximate shape and size of a specimen which is excised during a skin biopsy procedure The closure apparatus and method are effective for controlling bleeding, promoting healing, and reduce the likelihood of excessive scarring.

A further benefit, in the addition to the foregoing benefits, is that damage to the biopsy specimen is reduced because the biopsy procedure is performed with very little manipulation of the tissue.

In another aspect of the invention, a pre-cut sterile sponge is combined with a biopsy punch and a syringe.

The foregoing features and benefits of our invention, together with other features and benefits, will be apparent from the ensuing detailed description taken in conjunction with the accompanying drawings. The best mode which is contemplated in practicing our invention is disclosed and the subject matter in which exclusive property rights are claimed is set forth in each of the numbered claims which are appended to the detailed description.

BRIEF DESCRIPTION OF THE DRAWINGS

FIG. 1 is a plan view of an alternate embodiment in which a pre-cut sterile sponge is combined with a biopsy punch and syringe.

FIG. 2 is a front view of the alternate embodiment shown in FIG. 1.

FIG. 3 is a front view of the alternate embodiment shown in FIGS. 1 and 2 with the syringe portion removed.

FIG. 4 is a bottom view of FIG. 3.

FIG. 5 is a cross-sectional view taken on the line 5—5 in FIG. 3.

FIG. 6 is a cross-sectional view taken on the line 6—6 in FIG. 2.

DETAILED DESCRIPTION OF THE PREFERRED EMBODIMENT

Figure 10:
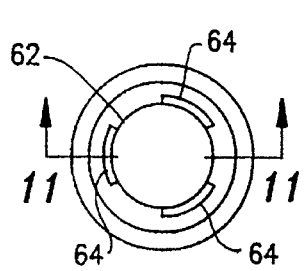
FIG. 10 is an enlargerd plan view of the biopsy punch and adapter of the alternate embodiment.
Figure 8:
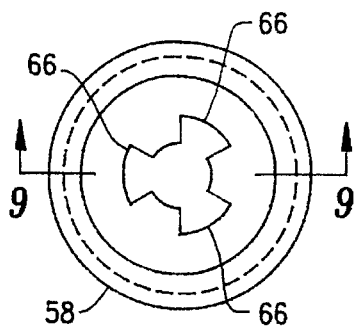
FIG. 8 is an enlarged plan view of the needle of the syringe.

Referring now to the drawings wherein like numerals designate like and corresponding parts throughout the several views, in FIGS. 1 through 13, inclusive, is illustrated, for purposes of describing our invention, a closure device for repair of resulting skin defect and controlling bleeding during a routine skin biopsy procedure with reduction of chances of inducing excessive scar tissue.

Referring now to FIGS. 1 through 13, inclusive, an alternate embodiment 65 is shown wherein a sterile sponge 34 is combined with a biopsy punch 52 and a syringe 53. The construction of the syringe 53 is generally depicted in FIGS. 19 and 20. The syringe 53 is comprised of a transparent body 54, a usual type plunger 55 which slidably engages body 54, a conventional needle 56, a detachable sterile cap 57, and an adapter 58 made from a rubber-like material. At the lower end of the plunger 55 there is the usual seal 59 made of a rubber like material. "One material for the sponge 34 which has been evaluated and found to be acceptable for practicing our invention is an absorbable gelatin sponge manufactured by the Upjohn Company under the registered trademark "GELFOAM". It is a water-insoluble, off-white, non-elastic, porous, pliable product made from purified pork skin gelatin USF granules and is available in the form of pads."

As best seen in FIGS. 6 through 9, the needle 56 is lightly press-fitted into one end of the adapater 58. The other end of the adapter 58 is lightly press-fitted to the lower end of the syringe's body 54 such that the adapter 58 can be removed from the body 54 by hand to expose the biopsy punch 52 which is mounted to the lower end of the body 54 by means of a second adapter 60.

Referring now to FIGS. 10 through 13, the biopsy punch 52 is press fitted into an aperture 61 in the center of the adapter 60 which is mounted to the lower end of the syringe's body 54. Optional adapters are provided to accomodate variations in biopsy punch diameter. The sterile sponge 34 is pre-assembled into the interior of the punch 52 together with a cylindrical plunger 62° The upper end of the plunger 62 contacts the syringe's plunger 55 when the syringe's plunger 55 is in the fully engaged position. The upper end of the punch 52 has a narrow flange 63 which locates and assists in retaining the punch 52 in the adapter 60.

Figure 12:
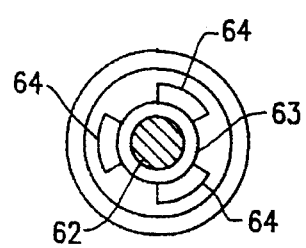
FIG. 12 is a cross-sectional view taken on the line 12—12 in FIG. 11.
Figure 11:
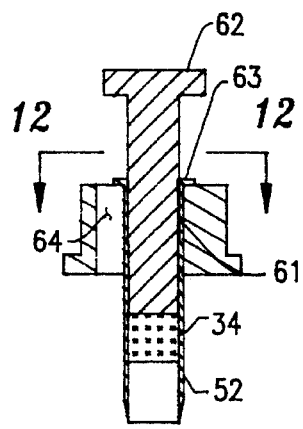
FIG. 11 is a cross-sectional view taken on the line 11—11 in FIG. 10.
Figure 13:
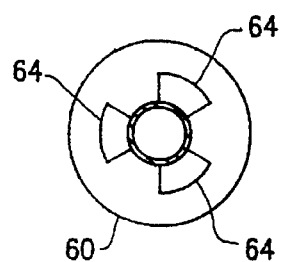
FIG. 13 is a bottom view of the biopsy punch and adapter.
Figure 9:
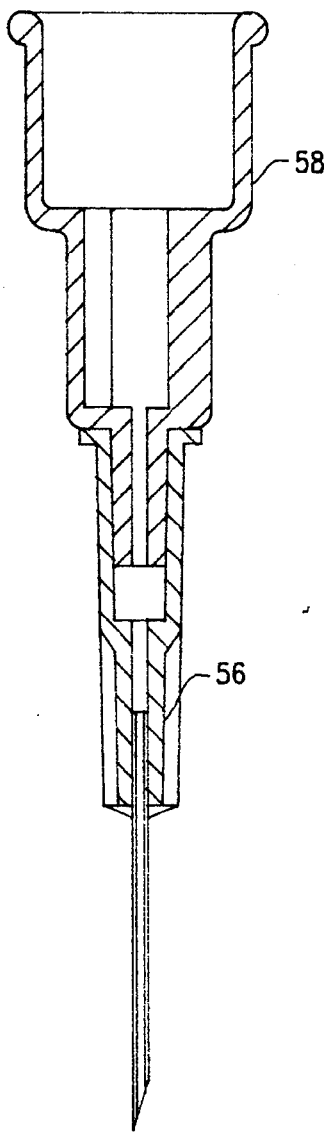
FIG. 9 is a cross-sectional view taken on the line 9—9 in FIG. 8.
Figure 7:
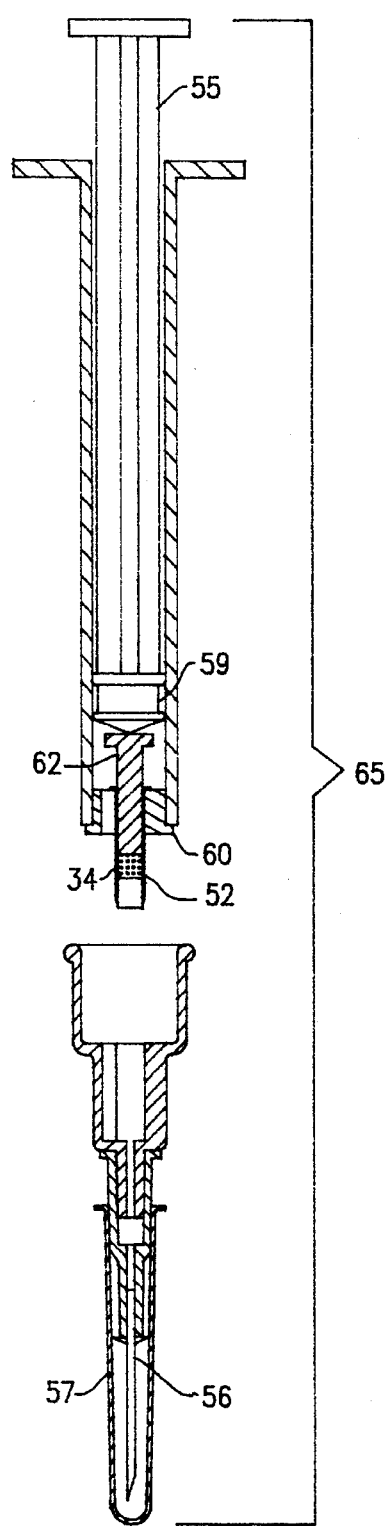
FIG. 7 is similar to FIG. 6 except showing the needle of the syringe and an adapter separated from the remainder of the closure device.

As best seen in FIGS. 11 and 12, extending axially through the punch adapter 60 are three fluid passages 64 which are aligned with three axial fluid passages 66 in the needle adapter 58. The fluid passages 64 and 66 allow fluid to by-pass the sterile sponge 34 and plunger 62 when the device is used as a syringe 53.

The manner of using this embodiment during a routine biopsy is as follows. The syringe 53 is filled with an anesthetic (not shown) by removing the sterile cap 57, inserting the needle 56 into the anethesthic and withdrawing the plunger 55 from the body 54. During the withdrawal of the plunger 55, liquid anesthetic is drawn through the needle 56, through the axial passages 64 of the adapter 60 and into the body 54 of the syringe 53.

The skin of the biopsy site is then pierced by the pointed end of the needle 56 and the plunger 55 is depressed to anesthetize the biopsy site. The needle 56 is then withdrawn and removed from the body 54 by detaching the adapter 58 and needle 56 from the end of the syringe's body 54. After the needle 56 has been removed, the biopsy punch 52 is pressed against the skin and rotated to excise a cylinder shaped sample for the biopsy.

The syringe's plunger 55 is then partially depressed to extract the sample from the punch 52. Thereafter the punch 52 is positioned against the wound and the syringe's plunger 55 is further depressed to implant the sterile sponge 34 into the wound.

After the sponge 34 has been implanted, pressure is applied to the sponge 34 by a conventional sterile cotton gauze (not shown) for approximately 30 to 60 seconds to terminate bleeding and seal the wound.

From the foregoing it will be understood that our invention provides an improved closure device and method for performing a routine biopsy procedure. Moreover, it will be appreciated that our improved closure device provides numerous benefits, among which are, a reduction in cost and time, reduced handling of tissue, and a reduction in the likelihood of inducing the formation of excessive scar tissue.

Although but several embodiments of our invention have been illustrated and described, it is not our intention to limit our invention to these embodiments since other embodiments can be provided by substitutions in materials and modifications in the shape, number and arrangements of parts and steps in our closure device and changes in steps in our method without departing from the spirit thereof.

We claim:

1. A closure device for the repair of skin tissue, controlling bleeding, and reducing the likelihood of inducing excess scar tissue, during a routine skin biopsy procedure, comprising: a syringe for administering an anesthetic to a biopsy site of a patient, said syringe having a detachable needle at one end of said body; a biopsy punch attached to a lower end portion of said body of said syringe, said biopsy punch being exposed for excising a biopsy specimen when said needle is detached from said body; and a pre-formed cylindrical sponge in the interior of said syringe having a diameter which is about the same diameter as the diameter of a circular blade of a punch used for excising a specimen of skin for a skin biopsy, said sponge being accessible when said detachable needle is removed from said syringe for implanting said sponge into a bleeding site after the excising of said specimen by said punch during a routine biopsy procedure.

2. The closure device recited in claim 1 wherein the diameter of said pre-formed cylindrical sponge is equal to the diameter of said circular blade of said punch.

3. The closure device recited in claim 1 wherein the diameter of said pre-formed cylindrical sponge is greater than the diameter of said circular blade of said punch.

4. The closure device recited in claim 1 wherein said sponge is a water-insoluble, non-elastic, porous and pliable product made from purified pork skin gelatin USP granules.

5. The closure recited in claim 1 wherein said sponge is diametrically pre-compressed when said sponge is in said interior of said punch.

6. The closure device recited in claim 1 wherein said tubular body of said syringe is transparent.

7. A closure device for repair of a tissue defect of a biopsy site and for controlling bleeding during a routine skin biopsy procedure with reduced chance of inducing excess scar tissue comprising, in combination: a syringe for administering an anesthetic to a biopsy site of a patient, said syringe having a body for holding an anesthetic and a detachable needle at one end of said body; a biopsy punch attached to a lower end portion of said body of said syringe, said biopsy punch being exposed for excising a biopsy specimen when said needle is detached from said body; and a sterile cylindrical sponge located in the interior of said biopsy punch, said sponge being made from a foam material which swells and is absorbed in a bleeding site with little tissue reaction and pre-formed to a diameter which approximately corresponds to the inside diameter of said biopsy punch; and a means for implanting said sterile sponge into a bleeding site after the excising of said specimen to control bleeding in said biopsy site.

8. A method for performing a skin biopsy procedure, said method comprising the steps of: administering an anesthetic with a syringe to a biopsy site of a patient; removing a detachable needle from one end of said syringe to expose a biopsy punch; excising a specimen of skin using said punch; implanting a cylindrical sponge stored in said syringe having about the same diameter as said biopsy punch into the wound caused by said excising of said specimen.

9. The method recited in claim 8 further comprising the step of applying pressure to said sponge for a short interval of time after said sponge has been implanted into said wound.

* * * * *